(12) United States Patent
Turrentine et al.

(10) Patent No.: US 10,409,953 B2
(45) Date of Patent: *Sep. 10, 2019

(54) BIO-SAMPLE COLLECTION KITS, SYSTEMS AND METHODS FOR GENERATING BIOMARKER DATA FOR USE IN DETERMINING AN INSURANCE SCORE

(71) Applicant: STATE FARM MUTUAL AUTOMOBILE INSURANCE COMPANY, Bloomington, IL (US)

(72) Inventors: David Turrentine, Bloomington, IL (US); Jeremy Myers, Normal, IL (US); Abby Tohline, Bloomington, IL (US); Angi Bobsin, Heyworth, IL (US); Kelly S. Minter, Normal, IL (US); Miranda Kemp, Bloomington, IL (US); Larry J. Ingrum, Mahomet, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 196 days.

This patent is subject to a terminal disclaimer.

(21) Appl. No.: 14/259,780

(22) Filed: Apr. 23, 2014

(65) Prior Publication Data

US 2015/0112718 A1 Apr. 23, 2015

Related U.S. Application Data

(63) Continuation of application No. 14/061,332, filed on Oct. 23, 2013, now Pat. No. 8,805,708.

(51) Int. Cl.
*G06F 19/00* (2018.01)
*G06Q 40/08* (2012.01)
(Continued)

(52) U.S. Cl.
CPC .......... *G06F 19/328* (2013.01); *A61B 5/1171* (2016.02); *A61B 5/150305* (2013.01); *A61B 5/150755* (2013.01); *A61B 10/0045* (2013.01); *G06Q 40/08* (2013.01); *G06Q 50/22* (2013.01); *A61B 5/117* (2013.01);
(Continued)

(58) Field of Classification Search
None
See application file for complete search history.

(56) References Cited

U.S. PATENT DOCUMENTS

| 5,879,453 A * | 3/1999 | Streeter | A61B 5/1172 118/31.5 |
| 2012/0107841 A1* | 5/2012 | McIntyre | G01N 33/564 435/7.92 |

(Continued)

*Primary Examiner* — Bennett M Sigmond
*Assistant Examiner* — Gregory S Cunningham, II
(74) *Attorney, Agent, or Firm* — Marshall, Gerstein & Borun LLP; Randall G. Rueth

(57) ABSTRACT

The present disclosure generally relates to bio-sample, such as a dried blood spot (DBS) sample, a breath sample, an endothelial sample, saliva sample, etc., collection kits and identity authenticating mechanisms for the sample donors. The present disclosure further relates to systems and methods for generating biomarker data using bio-sample analysis information and authenticating information. The biomarker data may be used to determine an insurance score.

20 Claims, 15 Drawing Sheets

(51) Int. Cl.
*A61B 5/15* (2006.01)
*G06Q 50/22* (2018.01)
*G16H 10/40* (2018.01)
*A61B 5/1171* (2016.01)
*A61B 5/151* (2006.01)
*A61B 5/117* (2016.01)
*G01N 1/00* (2006.01)
*A61B 10/00* (2006.01)

(52) U.S. Cl.
CPC ..... *A61B 5/150022* (2013.01); *A61B 5/15142* (2013.01); *A61B 5/150358* (2013.01); *A61B 5/150786* (2013.01); *A61B 10/0051* (2013.01); *A61B 2010/0087* (2013.01); *A61B 2503/12* (2013.01); *A61B 2560/0406* (2013.01); *G01N 2001/005* (2013.01); *G16H 10/40* (2018.01)

(56) References Cited

U.S. PATENT DOCUMENTS

2013/0041290 A1\* 2/2013 Kording ............... A61B 5/1101
          600/595
2013/0197934 A1\* 8/2013 Trifunov ................ G06Q 50/22
          705/3

\* cited by examiner

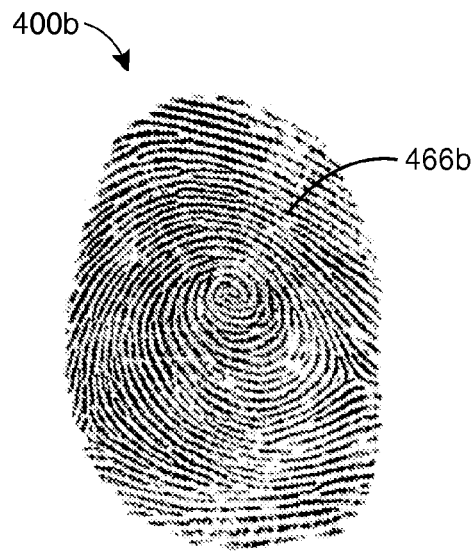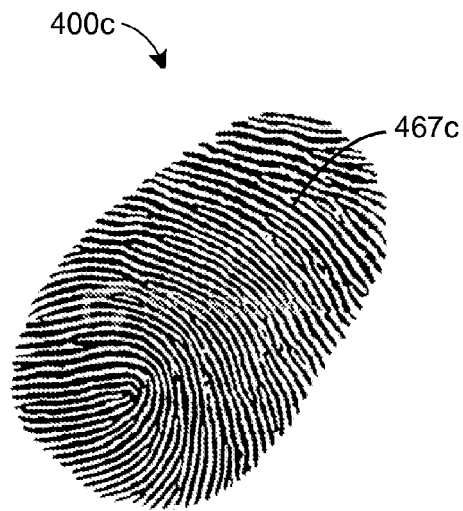
FIG. 4B    FIG. 4C
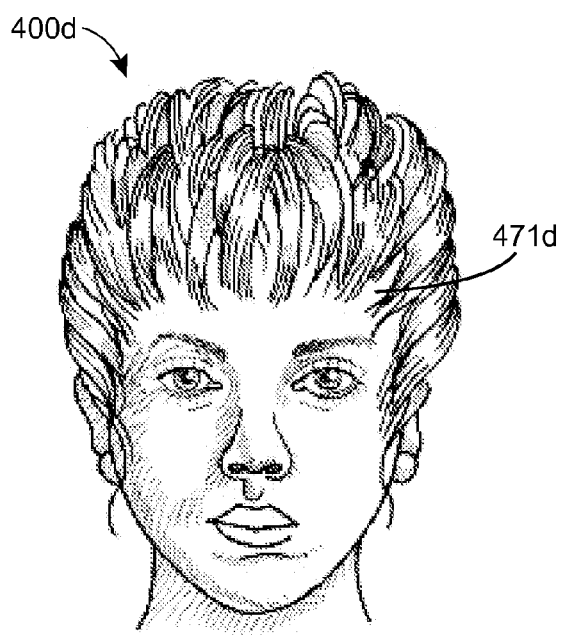
FIG. 4D

BIO-SAMPLE COLLECTION KITS, SYSTEMS AND METHODS FOR GENERATING BIOMARKER DATA FOR USE IN DETERMINING AN INSURANCE SCORE

RELATED APPLICATION

This application is a continuation of U.S. patent application Ser. No. 14/061,332, filed on Oct. 23, 2013, and entitled Bio-Sample Collection Kits, Systems and Methods for Generating Biomarker Data for Use in Determining an Insurance Score. The entire disclosure of which is incorporated herein by reference.

TECHNICAL FIELD

The present disclosure generally relates to bio-sample collection kits, such as dried blood spot (DBS) sample collection kits, breath sample collection kits, endothelial sample collection kits, saliva sample collection kits, etc., and automatic identity authenticating. More particularly, the present disclosure relates to generating biomarker data, that includes bio-sample analysis information and identity authenticating information, for use in determining insurance risk assessments.

BACKGROUND

Insurance risk assessment (or insurance scores) may be based, at least in part, on biomarkers associated with an individual seeking insurance coverage. The individual's life expectancy and, or expected health care needs may be correlated with the biomarkers.

Biomarkers may be derived from a bio-sample, such as a blood sample, a breath sample, an endothelial sample, a saliva sample, etc. For example, an individual seeking to acquire insurance coverage may visit a health care provider or clinician and the health care provider or clinician may obtain a bio-sample from the individual. The bio-sample may then be analyzed by a laboratory to determine associated biomarker information.

When a bio-sample is acquired by a health care provider, the health care provider may authenticate an identity of the individual providing the sample. Thereby, biomarker information, derived from the bio-sample, may be associated with the individual. The biomarker information may be used to determine an insurance risk for the individual.

SUMMARY

A computerized method is provided for generating insurance risk related data that is, at least partially, based on biomarker information. The method may include providing a bio-sample collection kit and receiving a bio-sample from an individual using the bio-sample collection kit. The method may also include automatically receiving, at a processor of a first computing device, identity authenticating data, wherein the identity authenticating data is representative of identity authenticating information that associates the bio-sample with the individual. The method may further include analyzing the bio-sample to determine the biomarker information and generating, using a processor of a second computing device, biomarker data, wherein the biomarker data is representative of the biomarker information and the identity authenticating information. The method may also include generating, using a processor of a third computing device, insurance risk related data that is based, at least in part, on the biomarker data and causing the processor of the third computing device to automatically store the insurance risk related data in a memory that is coupled to the processor in the third computing device.

In another embodiment, a system for collecting and storing insurance risk related data is provided that is, at least partially, based on biomarker information. The system may include a bio-sample collection kit, wherein the bio-sample collection kit is used to obtain a bio-sample from an individual and an identity authenticating data receiving module that, when executed on a processor of a first computing device, automatically receives identity authenticating data, wherein the identity authenticating data is representative of identity authenticating information that associates the bio-sample with the individual. The system may also include a biomarker data generation module that, when executed on a processor of a second computing device, generates biomarker data, wherein the biomarker data is representative of biomarker information, that is obtained from an analysis of the bio-sample, and the identity authenticating information. The system may further include an insurance risk data generating module that, when executed on a processor of a third computing device, generates insurance risk related data that is based, at least in part, on the biomarker data and an insurance risk related data storing module that, when executed by the processor of the third computing device, causes the processor of the third computing device to store the insurance risk related data in a memory that is coupled to the processor of the third computing device.

In yet another embodiment, a computer-readable storage medium is provided including non-transitory computer-readable instructions stored thereon and to be executed on a processor of a system for automatically collecting and storing insurance risk related data that is, at least partially, based on biomarker information. The stored instructions may include a biomarker information data receiving module that, when executed on a processor of a computing device, receives biomarker information that is based on an analysis of a bio-sample obtained from an individual using a bio-sample collection kit. The stored instructions may also include an identity authenticating data receiving module that, when executed on a processor of the computing device, automatically receives identity authenticating data, wherein the identity authenticating data is representative of identity authenticating information that associates the bio-sample with the individual. The stored instructions may further include a biomarker data generation module that, when executed on a processor of the computing device, generates biomarker data, wherein the biomarker data is representative of the biomarker information and the identity authenticating information.

BRIEF DESCRIPTION OF THE DRAWINGS

The figures described below depict various aspects of the systems and methods disclosed herein. It should be understood that each figure depicts an embodiment of a particular aspect of the disclosed systems and methods, and that each of the figures is intended to accord with a possible embodiment thereof. Furthermore, wherever possible, the following description refers to the reference numerals included in the following figures, in which features depicted in multiple figures are designated with consistent reference numerals.

FIGS. 4A-4D depict an example kiosk and authentication information that may be obtained using a kiosk;

DETAILED DESCRIPTION

An insurance risk assessment (or an insurance score) may be based, at least in part, on biomarker information associated with an individual seeking insurance coverage. Biomarker information may be derived from an analysis of at least one biological sample (or bio-sample), such as a blood sample, a breath sample, an endothelial sample, a saliva sample, etc., obtained from the individual seeking coverage. When a bio-sample is ascertained by a health care provider or clinician, the health care provider or clinician may authenticate an identity of the individual and manually associate the bio-sample with the individual. If, on the other hand, the individual obtains the bio-sample herself, there may be a need for automatically authenticating the identity of the individual.

The bio-sample collection kits, systems and methods for collecting a bio-sample of the present disclosure allow an individual seeking insurance coverage to ascertain their own bio-sample. The bio-sample collection kits, systems and methods for collecting a bio-sample of the present disclosure may include a mechanism, such as a fingerprint/hand print input device, an image input device, a heart rate monitoring input device, etc., for automatically authenticating an identity of an individual that uses the bio-sample collection kit to provide a bio-sample.

With recent advancements in technology, such as automatic fingerprint identification, automatic handprint identification, automatic deoxyribonucleic acid (DNA) identification, automatic heart rate/electrocardiogram identification, automatic retinal identification, automatic voice recognition, automatic image recognition, etc., it is becoming possible for a processor of a computing device to automatically authenticate an identity of an individual. A processor of a computing device of the present disclosure may automatically acquire identity authenticating information from any suitable input device, such as a fingerprint input device, a handprint input device, a deoxyribonucleic acid (DNA) input device, a heart rate/electrocardiogram input device, a retinal input device, a voice input device, an image input device, etc.

Figure 1:
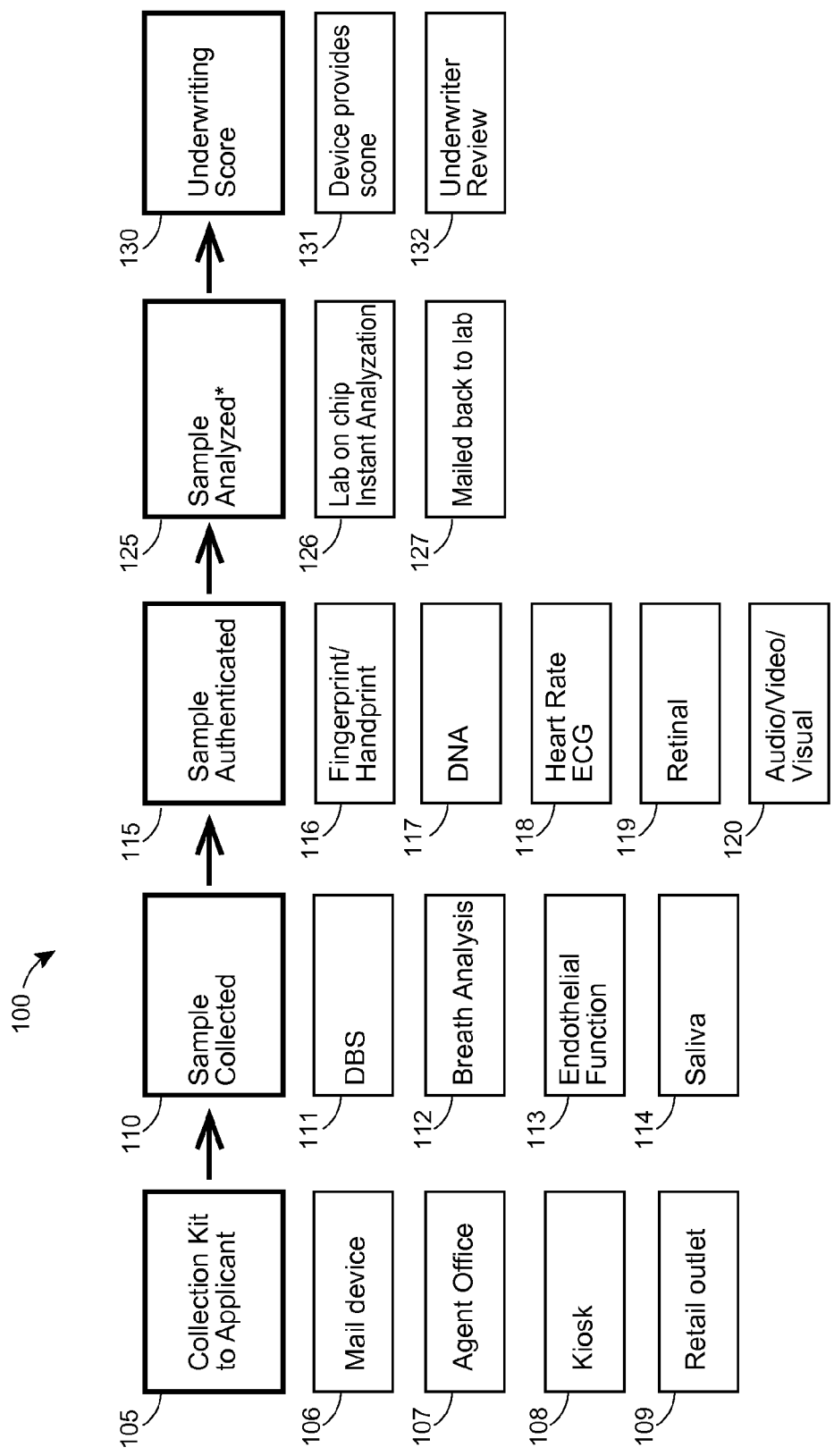
FIG. 1 depicts an example overview of various options for generating biomarkers for use in generating insurance underwriting scores.

Turning to FIG. 1, an example overview of various options for generating biomarkers 100 for use in generating an insurance underwriting score 130 are depicted. For example, a bio-sample collection kit 105 may be provided to an individual seeking insurance coverage via mailing the bio-sample collection kit to the individual 106, mailing the bio-sample collection kit to an insurance Agent 107, dispensing the bio-sample collection kit to the individual via a kiosk 108 or delivering the bio-sample collection kit to the individual at a retail outlet 109. While only mailing the bio-sample collection kit to the individual 106, mailing the bio-sample collection kit to an insurance Agent 107, dispensing the bio-sample collection kit to the individual via a kiosk 108 and delivering the bio-sample collection kit to the individual at a retail outlet 109 are depicted in FIG. 1, it should be understood that any method of providing the bio-sample kit 105 to an individual seeking insurance coverage may be employed within the context of the present disclosure. In any event, the individual seeking insurance coverage may select a desired option for receiving the bio-sample collection kit 105 while completing an application for insurance coverage.

The bio-sample collection kit 105 may be used to collect at least one bio-sample 110. For example, a dried blood spot (DBS) sample 111 may be collected, a breath sample 112 may be collected, an endothelial sample 113 may be collected or a saliva sample 114 may be collected. While only a dried blood spot (DBS) sample 111, a breath sample 112, an endothelial sample 113 and a saliva sample 114 are depicted in FIG. 1, it should be understood that any bio-sample 110 may be collected and used, within the context of the present disclosure, to generate an insurance score 130.

An identity of an individual seeking insurance coverage may be automatically authenticated 115. For example, authenticating information may be automatically obtained from at least one of a fingerprint/hand print of the individual 116, deoxyribonucleic acid (DNA) of the individual 117, a heart rate electrocardiogram (ECG) of the individual 118, retinal characteristics of the individual 119 and voice characteristics/visual characteristics of the individual 120. As described in conjunction with FIGS. 3A-3D, for example, various sensors, such as a fingerprint/hand print sensor, a deoxyribonucleic acid (DNA) sensor, a heart rate electrocardiogram (ECG) sensor, an audio sensor or an image sensor may be provided within a kiosk to automatically acquire identity authenticating information. While only a fingerprint/hand print of the individual 116, deoxyribonucleic acid (DNA) of the individual 117, a heart rate electrocardiogram (ECG) of the individual 118, retinal characteristics of the individual 119 and voice characteristics/visual characteristics of the individual 120 are depicted in conjunction with FIG. 1, it should be understood that any automatically obtained identity authenticating information 115 may be used, within the context of the present disclosure, to authenticate the identity of an individual providing a bio-sample 110. Alternatively, authenticating information 115 may be obtained via a face-to-face verification between an individual 116, for example, with an approved form of identification (e.g., a Driver's license).

The bio-sample 110 may be analyzed using either a laboratory on a chip 126 or a remote laboratory 127 to obtain biomarker information 125. While only a laboratory on a chip 126 and a remote laboratory 127 are shown in FIG. 1 to obtain biomarker information, it should be understood that any method of analyzing the bio-sample 110 may be employed within the context of the present disclosure to obtain biomarker information. The biomarker information 125 may be representative of at least one of: Albumin; Alkaline Phosphatase; ALT (SGPT); AST (SGOT); Bilirubin (Total); BUN (Blood Urea Nitrogen); Cholesterol; HDL Cholesterol; LDL Cholesterol; Cholesterol/HDL Ratio; LDL/HDL Ratio; Creatinine; Fructosamine; GGT/GGTP; Globulin; Glucose; HIV-1; Total Protein; Triglycerides; CDT; hemoglobin Hb A1c; tobacco use; illicit drug use; Hepatitis B Surface Ag; Hepatitis Be Ag; Hepatitis C Ab; NT-Pro BNP; and PSA.

It should be understood that other biomarker information 125 may be used within the context of the present disclosure to determine an insurance score 130. For example, as described in conjunction with FIG. 5, a device 131 (e.g., processor 555) may determine an insurance score 130 based, at least in part, on the biomarker information 125. Alternatively, or additionally, an underwriter review 132 may be used to, at least in part, determine an insurance score 130.

Figure 2A:
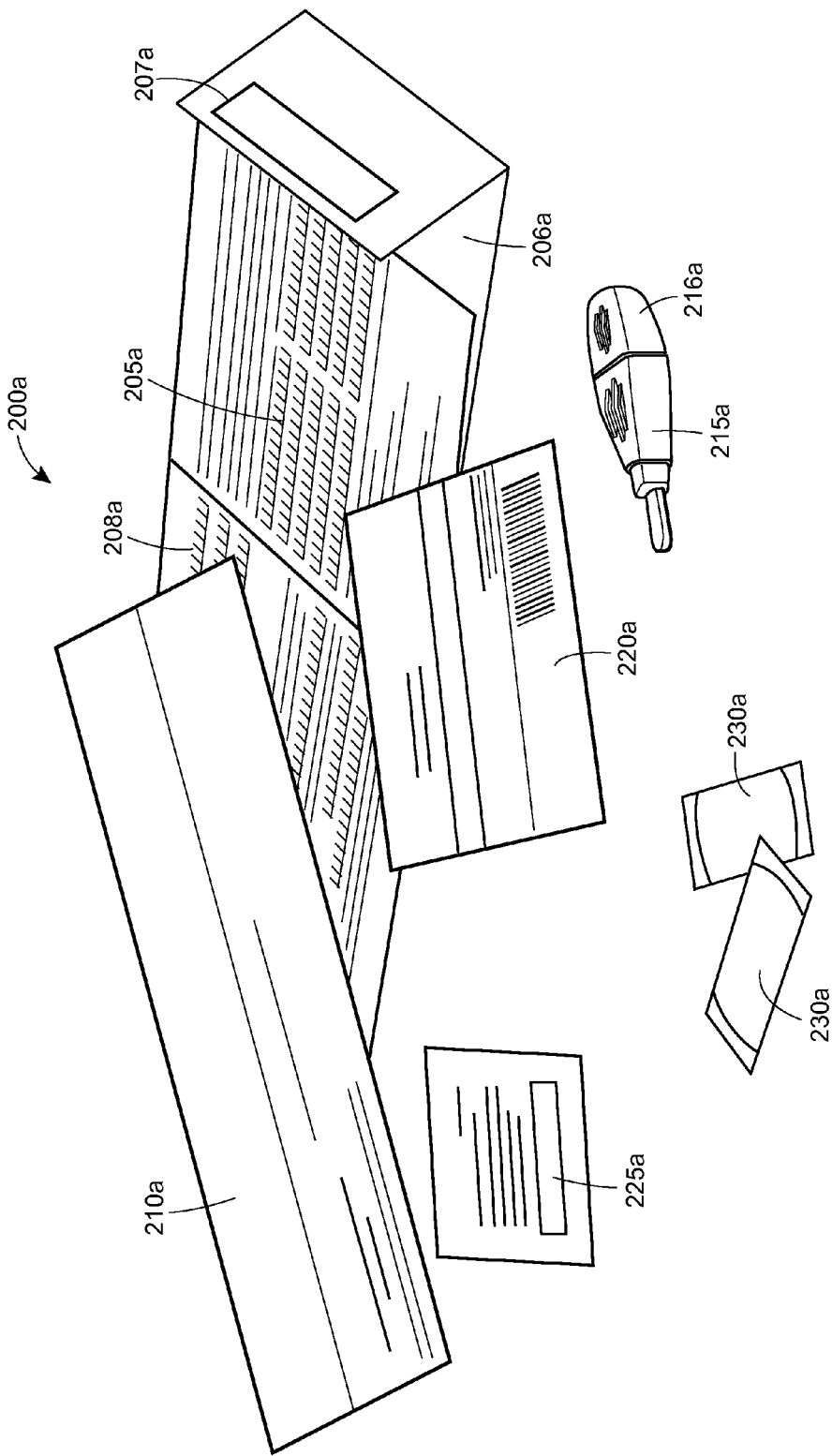
FIGS. 2A-2F depict an example dried blood spot (DBS) kit and obtaining a sample using the kit.

With reference to FIGS. 2A-2F, an example dried blood spot (DBS) kit 200a, 200b, 200e, along with illustrations 200c, 200d, 200f related to obtaining a bio-sample 110 using the kit 200a, 200b, 200e, are depicted. As depicted in FIG. 2A, a dried blood spot kit 200a may include a dried blood spot sample card 205a having filter paper 206a, a sample cover tab 207a and information entry areas 208a. The filter paper 206a may be defined by a plurality of individual pieces of filter paper with each piece of filter paper being identified by an outline, such as a circular outline, for example. In any event, the filter paper 206a may be a fleece material with a weight per surface area of approximately 60 g/m². It should be understood that the filter paper 206a may be any suitable material for receiving capillary blood 237d.

Figure 2B:
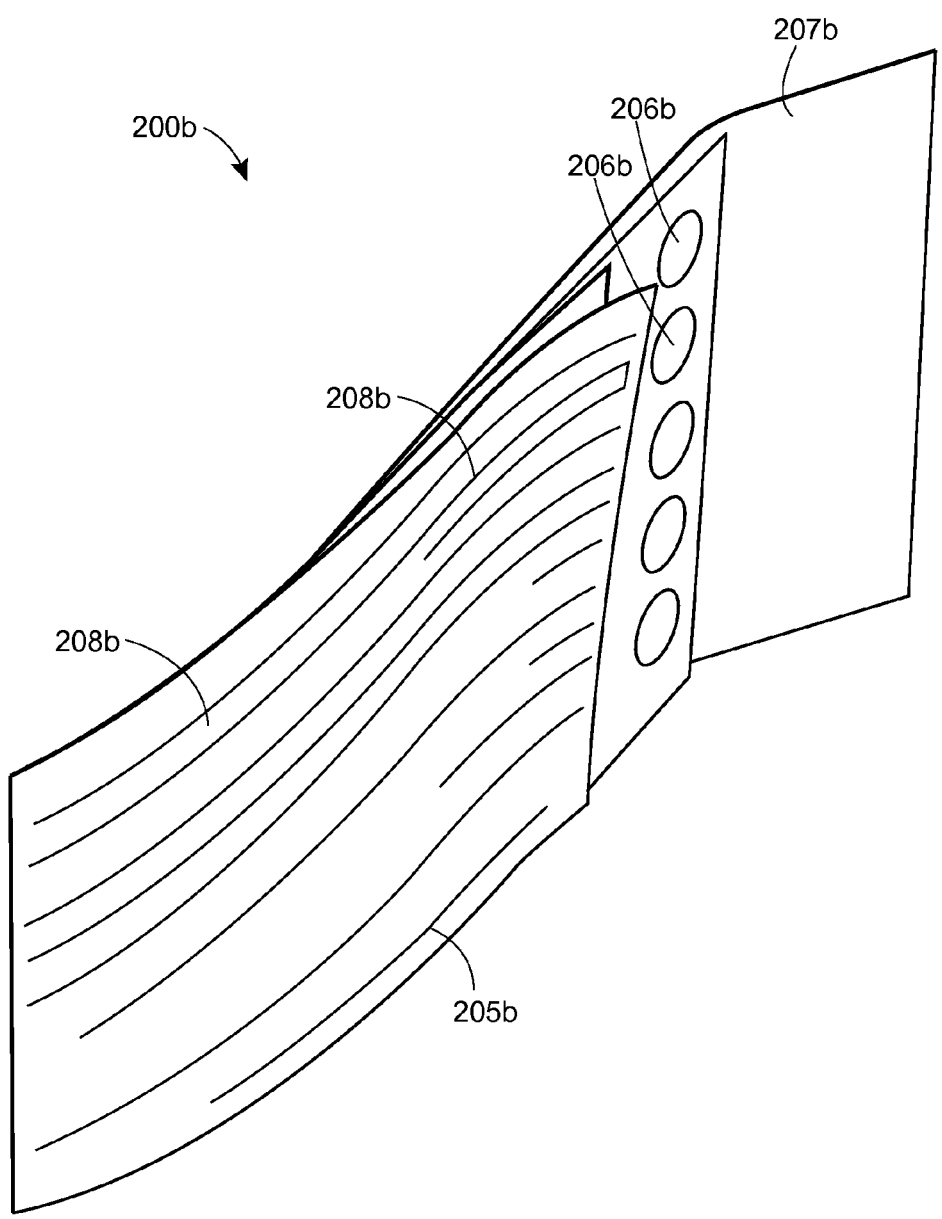

The dried blood spot sample kit 200a may further include an envelope 210a that may be used for mailing the dried blood spot sample card 205a to a laboratory. The envelope 210a may be made from a low gas-permeability material. The dried blood spot sample kit 200a may also include a lancet 215a having a handle 216a, a sterilizing gauze 220a, a desiccant package 225a and bandages 230a. The handle 216a may include a material, or sensor device, that automatically acquires a fingerprint, or series of fingerprints, any time a first finger 241c or a second finger 242c, for example, makes contact with the handle 216a. FIG. 2B depicts an enlarged view of a dried blood sample card 205b that may be included in a dried blood sample kit 200b. As depicted in FIG. 2B, the dried blood sample card 205b may include filter paper 206b, a sample cover tab 207b and information entry areas 208b.

Figure 2C:
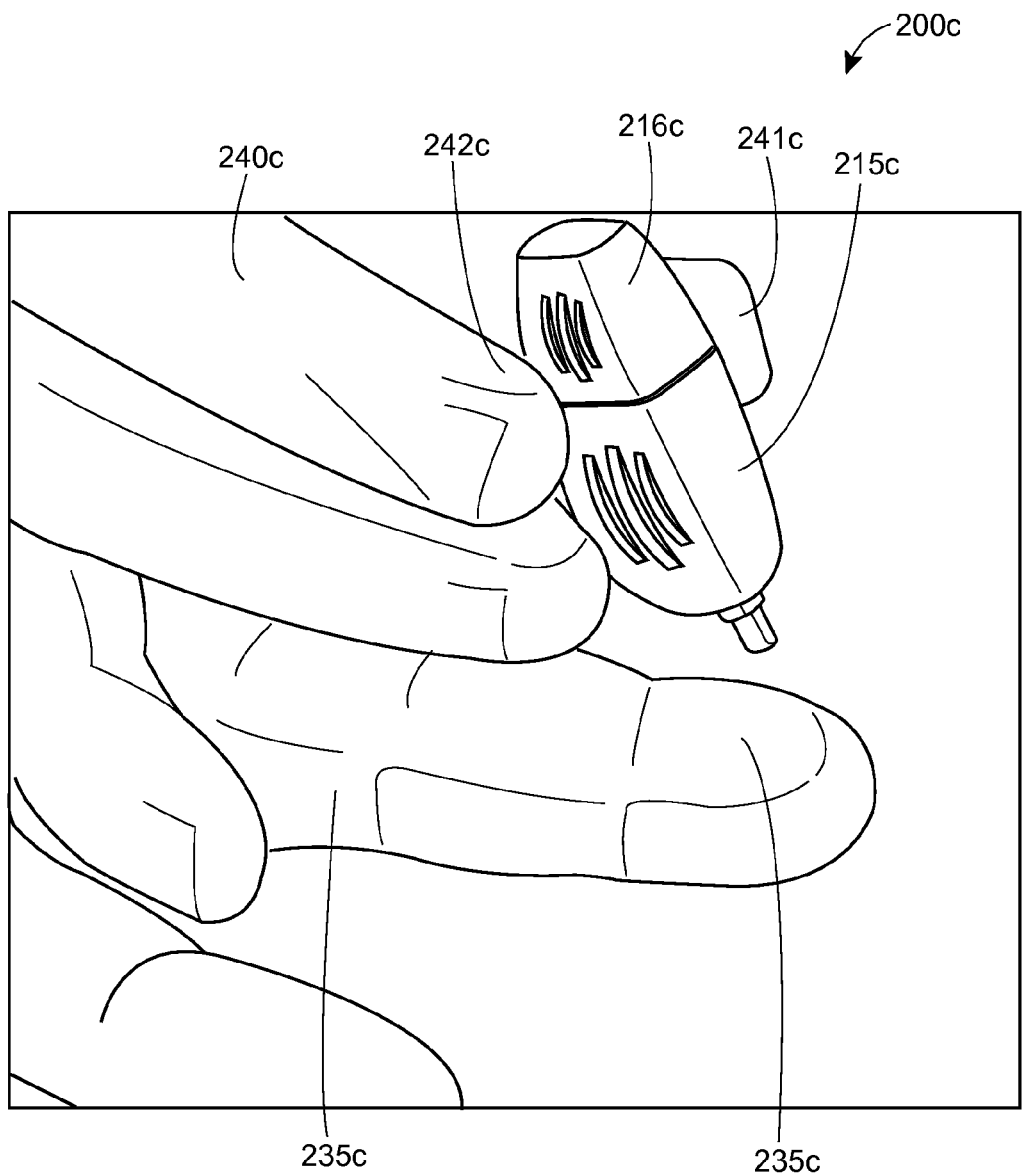
Figure 2D:
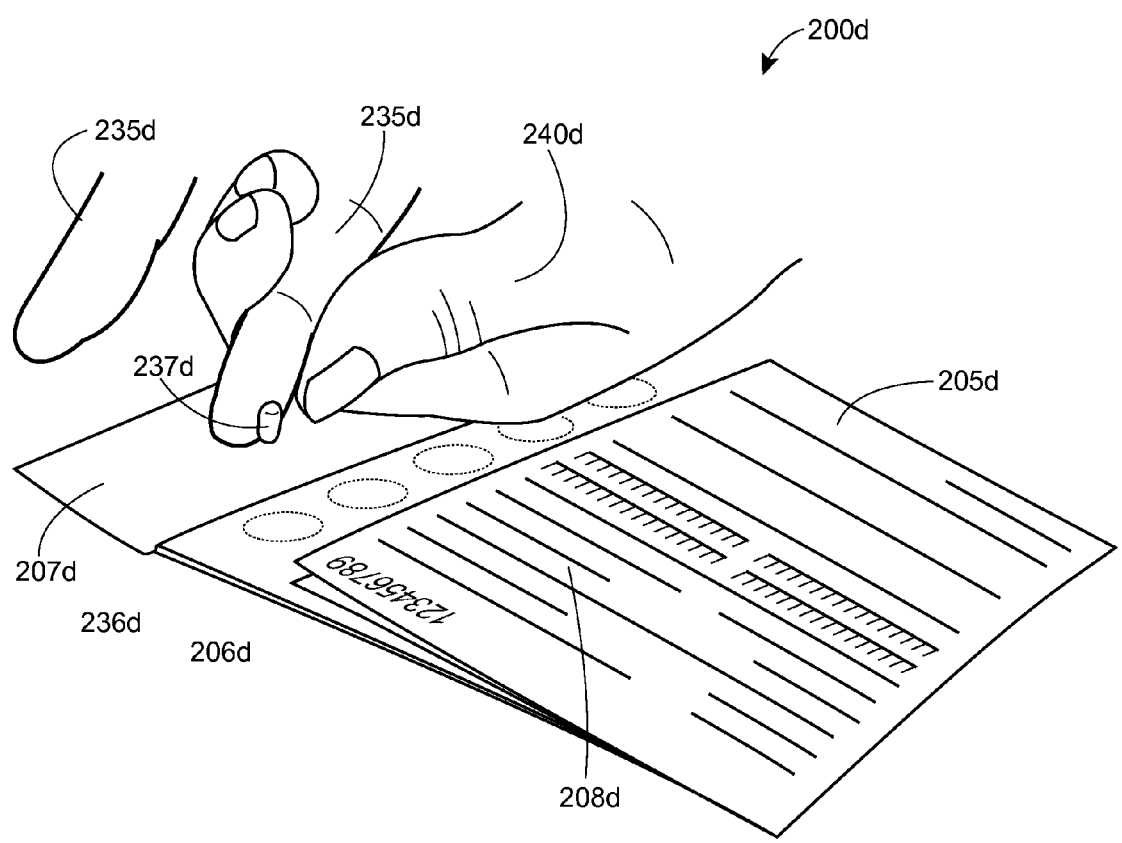
Figure 2E:
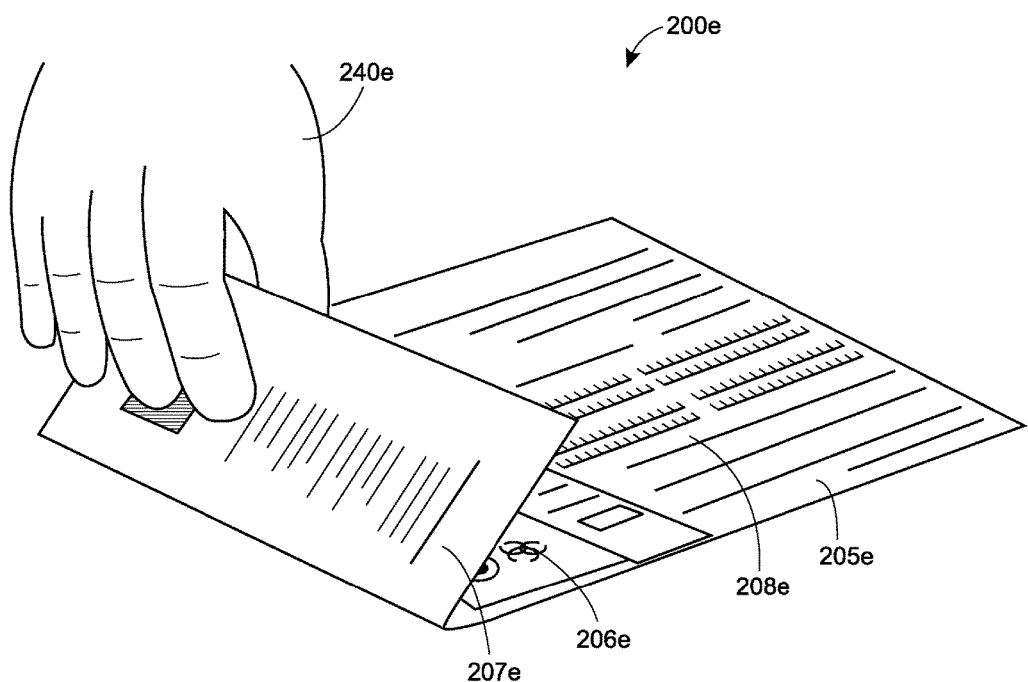

FIGS. 2C-2E illustrate a first hand 235c, 235d and a second hand 240c, 240d, 240e of an individual seeking insurance coverage 200c, 200d, 200e providing a capillary blood sample 237d. As illustrated in FIG. 2C, the individual seeking insurance coverage 200c holds a lancet 215c, via a handle 216c, using her first finger 241c and second finger 242c. The individual may prick her finger 236c using the lancet 215c. The individual 200d then may squeeze her finger 236d of her first hand 235d using her second hand 240d to deposit capillary blood 237d onto the filter paper 206d of the dried blood sample card 205d. The individual 200d, 200e may provide personal information within information entry area 208d, 208e, 208f.

Figure 2F:
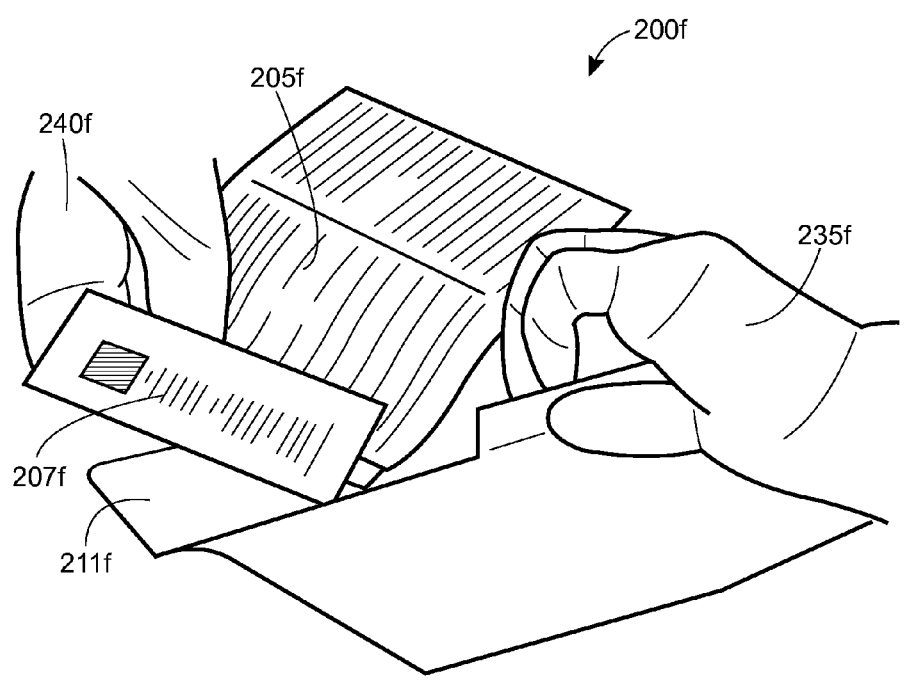

As depicted in FIG. 2F, once the capillary blood 237d has dried, the individual may fold over the cover tab 207d, 207e, 207f, using her hand 240f, to protect the dried blood sample 206e on the dried blood sample card 205f. The individual may then fold open an envelope tab 211f of the envelope 210f and insert the dried blood sample card 205f into the envelope 210f using her hand 235f. Subsequently, the individual may fold over the envelope tab 211f and seal the dried blood sample card 205f within the envelope 210f.

While FIGS. 2C and 2E illustrate obtaining capillary blood 237d from a finger 236d, a dried blood spot (DBS) sample 206e may be derived from capillary blood 237d that is obtained from an individual by pricking their heel or toe (not shown in FIGS. 2A-2E) with a lancet 215c. The capillary blood 237d may be blotted onto filter paper 206a. The capillary blood 237d may then be allowed to air dry on the filter paper 206d. Dried blood spot samples 206e are then analyzed to determine the biomarker information 125.

Alternatively, a bio-sample collection kit 205a may include a lab-on-chip device having an integral lancet 215a and handle 216a. An individual may use the lab-on-chip device to acquire a bio-sample 110 and automatically acquired authenticating information 115. In this event, the lab-on-chip device may be mailed or delivered to an insurance provider and the insurance provider may generate biomarker data from the bio-sample 110 and the authenticating information 115.

Figure 3:
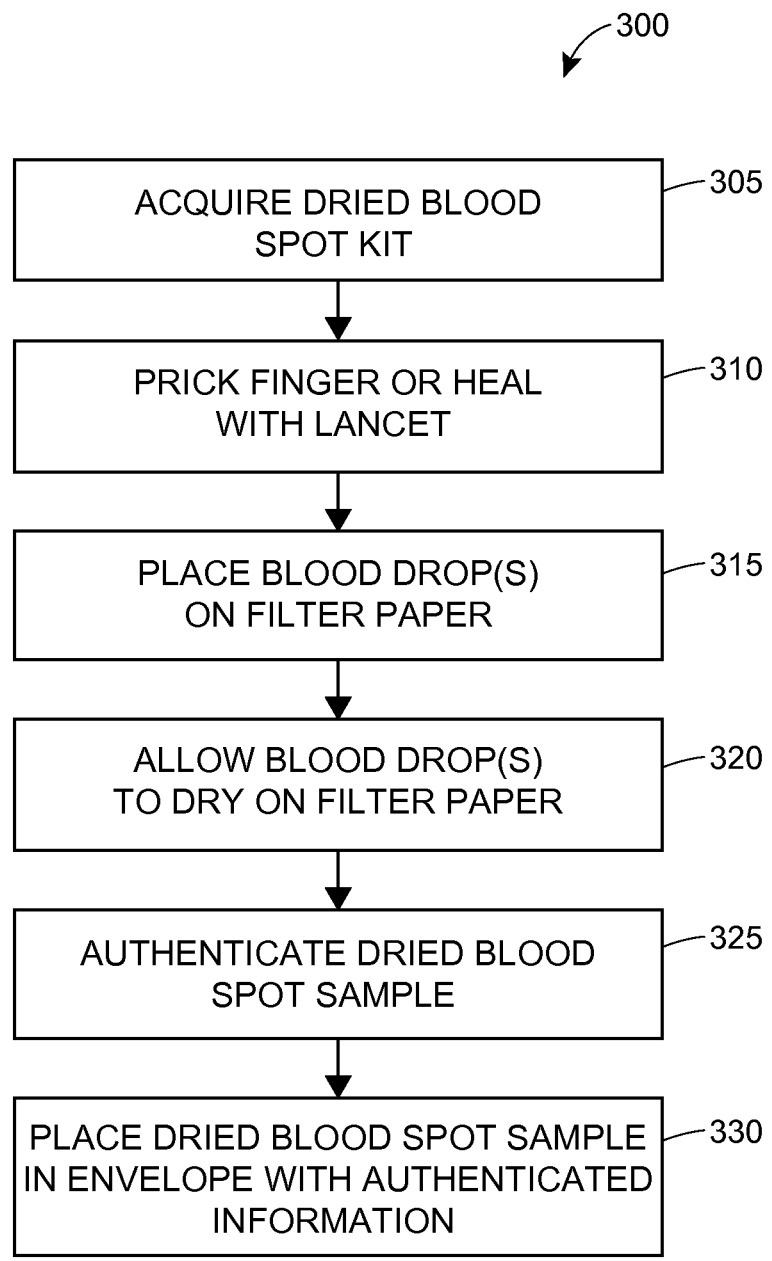
FIG. 3 depicts an example method for obtaining a dried blood sample.

With reference to FIG. 3, an example method for providing a dried blood sample 300 is depicted, that may be performed by an individual 200c seeking insurance coverage, using a dried blood spot sample kit 200a. A dried blood spot sample kit 200a may be provided to the individual 200c (block 305). The individual 200c may prick their finger 236c using a lancet 215c (block 310). The individual 200d may place a capillary blood drop 237d on the filter paper 206d (block 315). The capillary blood drop 237d may be air dried (block 320). The identity of the individual 200c may be authenticated (block 325) based on, for example, fingerprints 116 on a lancet handle 216a. The dried blood spot sample card 205e may be placed in an envelope 210a along with authenticating information 116 (e.g., the lancet 215c with finger prints on the lancet handle 216c) (block 330).

Figure 4A:
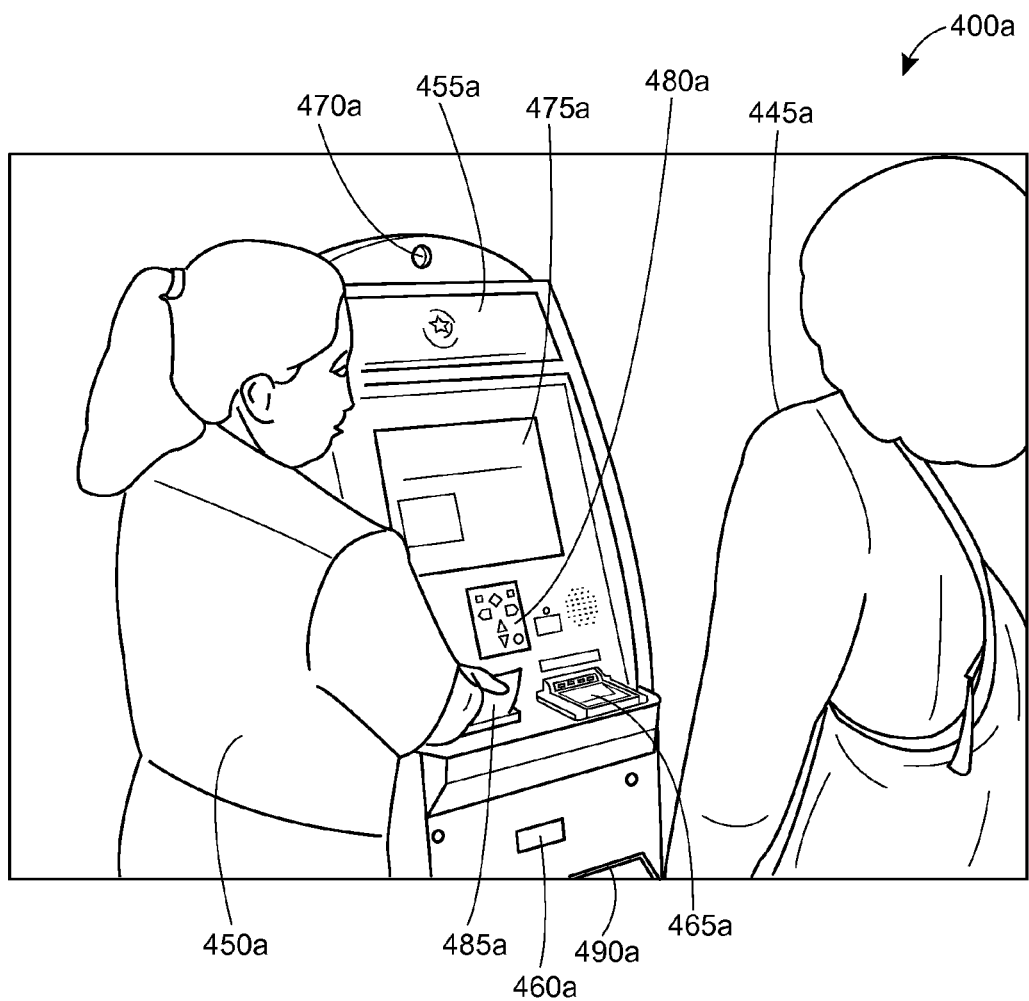

Turning to FIGS. 4A-4D, an example kiosk 455a is depicted within a retail outlet 400a. As depicted in FIG. 4A, an individual seeking insurance coverage 445a may cooperate with a kiosk attendant 450a to provide a bio-sample 110 via the kiosk 455a. Alternatively, the individual seeking insurance coverage 455a may provide the bio-sample 110 by herself. The individual 445a and/or the kiosk attendant 450a may operate the kiosk 455a via a display 475a and an operator input device 480a. The kiosk 455a may include a bio-sample collection kit dispenser 460a, 490a a fingerprint/hand print sensor 465a and a camera 470a. The bio-sample collection kit dispenser 460a may dispense a bio-sample collection kit 105 (e.g., a dried blood spot sample collection kit 205a). The individual 445a may provide a bio-sample 110 using the bio-sample collection kit 105 via the method 300. A processor (e.g., processor 525 of FIG. 5) may automatically acquire authenticating information 115 from the fingerprint/hand print sensor 465a and/or the camera 470a. For example, the processor 525 may acquire a finger print 400b, 400c, 466b, 467c and/or an image 400d, 471d of the individual 445a while the individual 445a is providing the bio-sample 110. Once the individual 445a provides the bio-sample 110, the bio-sample 110 may be deposited within a kiosk deposit 485a. The processor 525 may automatically associate the bio-sample 110 with the authenticating information 115 when the individual 445a deposits the bio-sample 110 into the kiosk deposit 485a.

Figure 5:
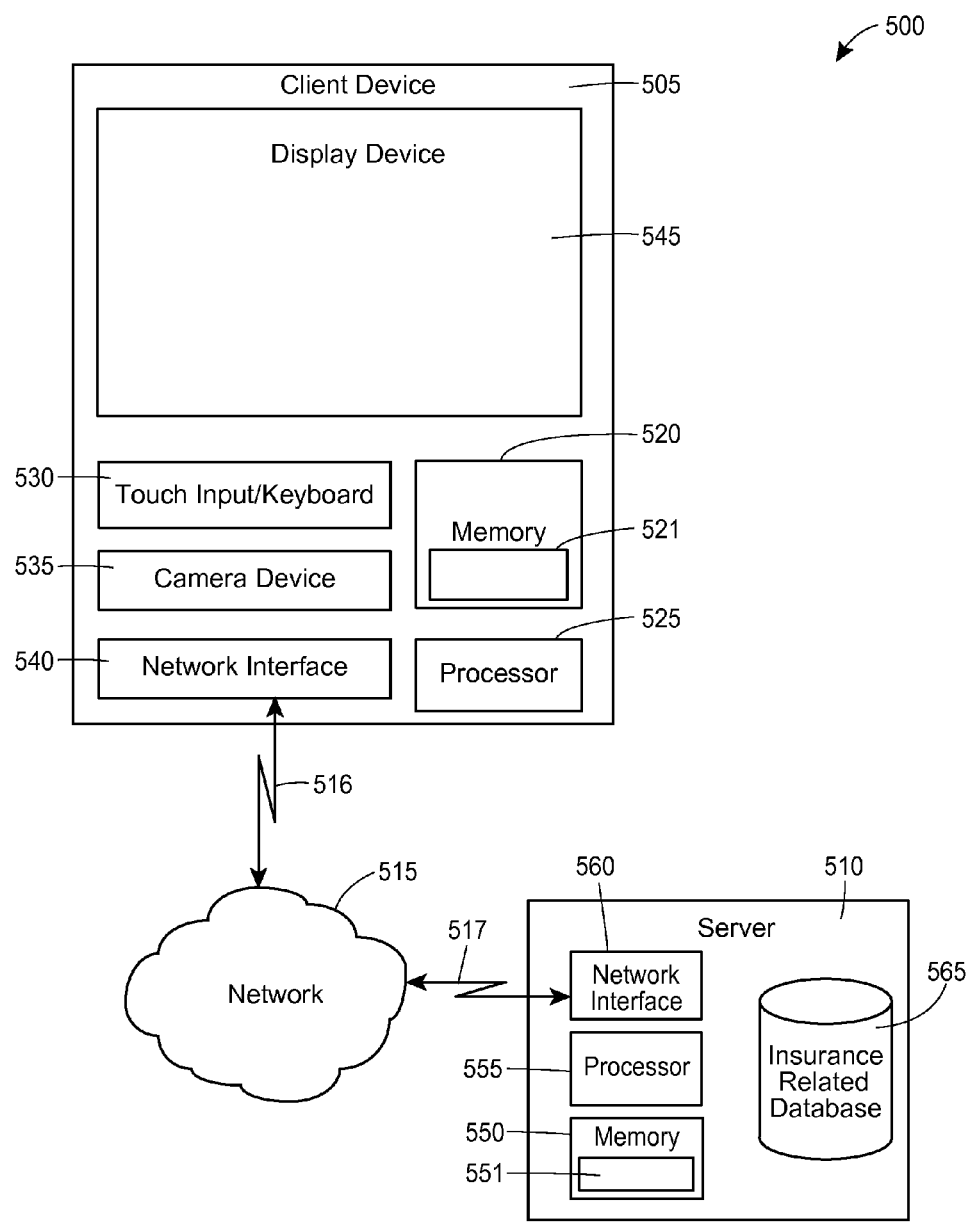
FIG. 5 depicts a high-level block diagram of an example system for obtaining biomarker data for use in determining insurance underwriting scores.

The details associated with a computer system 500 for obtaining a bio-sample 110 and for generating insurance risk (or insurance score) data 130 are now described beginning with reference to FIG. 5. FIG. 5 depicts a high-level block diagram of a computer system 500 that implements communications between a client device 505 (e.g., a kiosk 455a) and a remote computing device 510 to provide insurance score data 130 to an insurance related database 565. The client device 505 may be communicatively coupled to the remote computing device 510 via a network 415.

For clarity, only one client device 505 is depicted in FIG. 5. While FIG. 5 depicts only one client device 505, it should be understood that any number of client devices 505 may be supported and that each client device 505 may be any appropriate computing device, such as a kiosk 455a. The client device 505 may include a memory 520 and a processor 525 for storing and executing, respectively, a module 521. The module 521, stored in the memory 520 as a set of computer-readable instructions, may be related to a bio-sample collection application that, when executed on a processor 525, causes biomarker related data to be stored in the memory 520. As described in detail herein, the module 521 may facilitate interaction between the client device 505 and the remote computing device 510.

The processor 525, further executing the module 521, may facilitate communications between the computing device 510 and the client device 505 via a network interface 540, a client device network connection 516 and the network 515. The client device 505 may include a camera device 535. The processor 525, executing the module 521, may, for example, automatically acquire an image, or series of images, of an individual 445a while the individual 445a is providing a bio-sample 110. The client device 505 may further include a fingerprint/hand print device 465a, a microphone (a voice input device), a heart rate input device, a breath input device or any other suitable identity authenticating input device that is capable of providing authenticating information 115. The processor 525 may automatically acquire identity authenticating information 115 from an individual 445a via any suitable identity authenticating input device.

The client device 505 may include a display device 545 which may be any type of electronic display device such as a liquid crystal display (LCD), a light emitting diode (LED) display, a plasma display, a cathode ray tube (CRT) display, or any other type of known or suitable electronic display. The display device 545 may exhibit a display which depicts a user interface for assisting an individual 345a in providing a bio-sample 110. The client device 505 may include a user input device 530, such as a touch input/keyboard/pointing device (e.g., a mouse) that provides a mechanism for a user (e.g., an individual 445a or attendant 450a) of the client device 505 to launch a bio-sample collection application, to enter related information and to manually enter personal related data, such as insurance application information. The user input device 530 may be configured as an integral part of a display device 545, such as a touch screen display device. The network interface 540 may be configured to facilitate communications between the client device 505 and the remote computing device 510 via any hardwired or wireless communication network 515, including for example a hardwired Ethernet connection or a wireless LAN, MAN or WAN, WiFi, the Internet, or any combination thereof. Moreover, the client device 505 may be communicatively connected to the remote computing device 510 via any suitable communication system, such as via any publicly available or privately owned communication network, including those that use wireless communication structures, such as wireless communication networks, including for example, wireless LANs and WANs, satellite and cellular telephone communication systems, etc.

The computing device 510 may include a memory 550 and a processor 555 for storing and executing, respectively, a module 551. The module 551, stored in the memory 450 as a set of computer-readable instructions, may facilitate applications related to determining insurance risk (or insurance score) related data 130 based, at least in part, on biomarker information 125. The module 551 may also facilitate communications between the computing device 510 and the client device 505 via a network interface 560, a remote computing device network connection 517 and the network 515 and other functions and instructions.

The computing device 510 may be communicatively coupled to an insurance related database 565. While the insurance related database 565 is shown in FIG. 5 as being communicatively coupled to the remote computing device 510, it should be understood that the insurance related database 565 may be located within separate remote servers (or any other suitable computing devices) communicatively coupled to the remote computing device 510. Optionally, portions of insurance related database 565 may be associated with memory modules that are separate from one another, such as a memory 520 of the client device 505.

Figure 6:
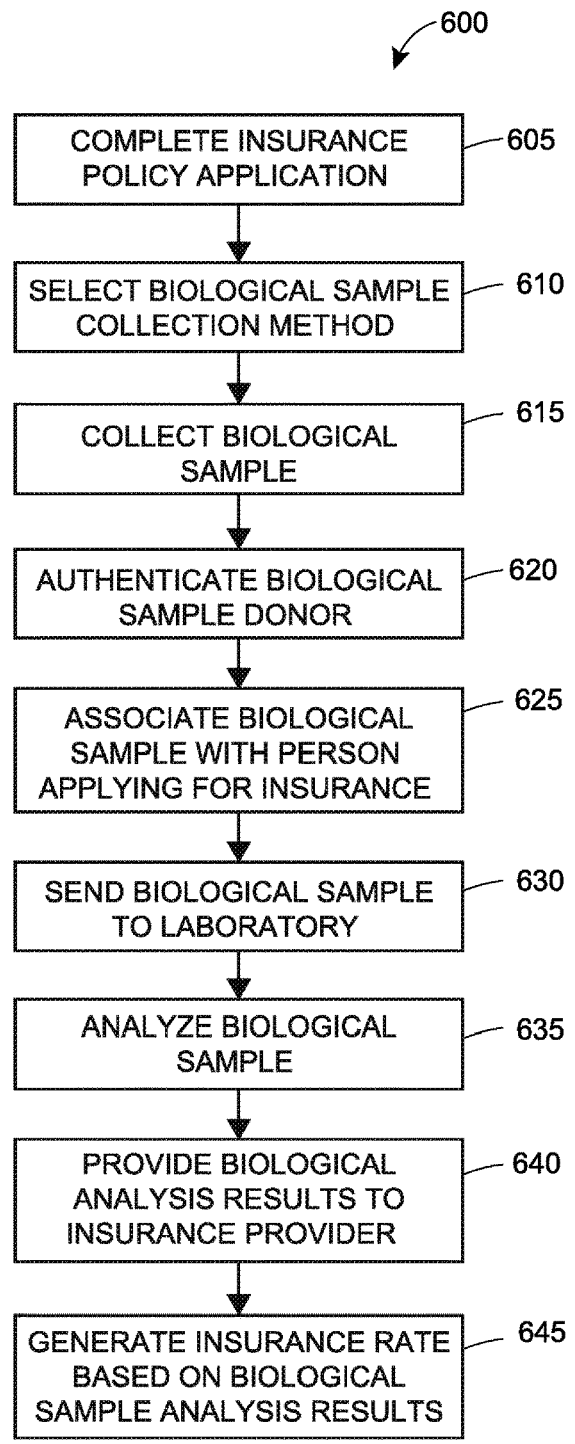
FIG. 6 depicts an example method of obtaining biomarker data for use in determining insurance underwriting scores.

Turning to FIG. 6, an example method of obtaining biomarker data for use in determining insurance underwriting scores 600 is depicted. A portion of the method 600 (e.g., blocks 605, 610, 615, 630) may be performed by an individual 445a seeking to obtain insurance coverage. A first processor (e.g., processor 525 of FIG. 5) may perform a portion of the method 600 (e.g., blocks 620, 625). A second processor (e.g., processor 555 of FIG. 5) may perform a portion of the method 600 (e.g., block 645). In any event, an individual 445a may complete an insurance policy application (block 605). The individual 445a may select a bio-sample collection method (block 610). For example, the individual 445a may select to have a bio-sample collection kit mailed to them at home 106, select to visit an insurance Agent's office to obtain a bio-sample collection kit 107, select to visit a kiosk to obtain a bio-sample collection kit 108 or may select to visit a retail outlet to pick-up a bio-sample collection kit 109.

The individual 445a may collect a bio-sample 110 (block 615). For example, a dried blood spot (DBS) sample 111 may be collected, a breath sample 112 may be collected, an endothelial sample 113 may be collected or a saliva sample 114 may be collected. The processor 525 may automatically authenticate the identity 115 of the individual 445a (block 620). For example, authenticating information may be automatically obtained from of at least one of a fingerprint/hand print of the individual 116, deoxyribonucleic acid (DNA) of the individual 117, a heart rate electrocardiogram (ECG) of the individual 118, retinal characteristics of the individual 119, voice characteristics/visual characteristics of the individual 120, or any other suitable identifying characteristic of the individual 445a. The processor 525 may automatically associate the bio-sample 110 with the individual 445a based on the authenticated identity information 115 (block 625).

The individual 445a may mail or deliver the bio-sample 110 to a laboratory (block 630). Alternatively, an insurance Agent, a kiosk attendant 450a, a retail outlet employee may deliver or mail the bio-sample 110 to a laboratory (block 630). A laboratory employee may analyze the bio-sample 110 to determine biomarker information 125 (block 635). A laboratory employee may provide the biomarker information 125 to an insurance provider (block 640). The biomarker information 125 may be representative of at least one of: Albumin; Alkaline Phosphatase; ALT (SGPT); AST (SGOT); Bilirubin (Total); BUN (Blood Urea Nitrogen); Cholesterol; HDL Cholesterol; LDL Cholesterol; Cholesterol/HDL Ratio; LDL/HDL Ratio; Creatinine; Fructosamine; GGT/GGTP; Globulin; Glucose; HIV-1; Total Protein; Triglycerides; CDT; hemoglobin Hb A1c; tobacco use; illicit drug use, Hepatitis B Surface Ag; Hepatitis Be Ag; Hepatitis C Ab; NT-Pro BNP; PSA or any other suitable biomarker. The processor 555 may generate insurance risk (or insurance score) data 130 based, at least in part, on biomarker data that is representative of the biomarker information 125 and the authenticating information 115 (block 645).

Figure 7A:
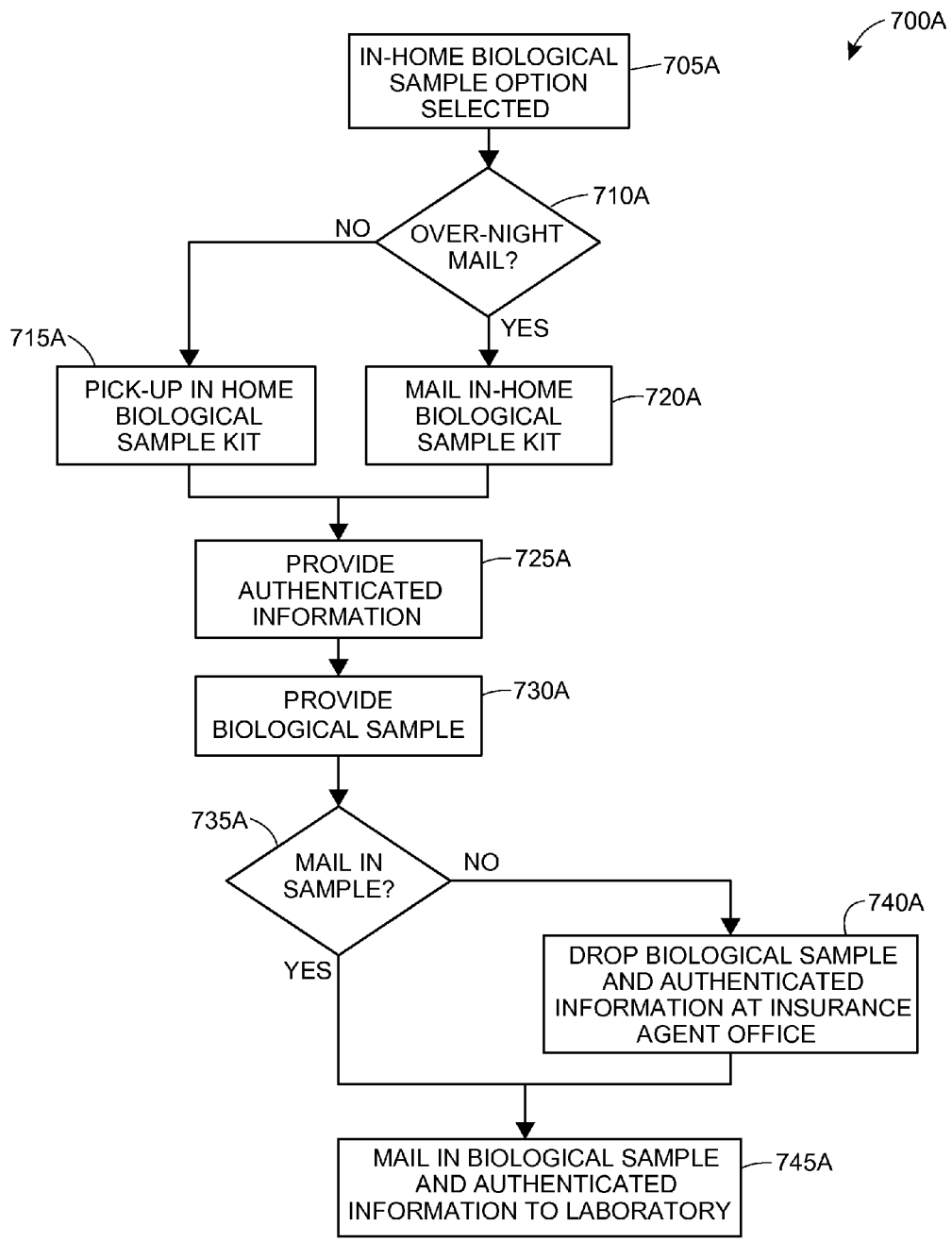
FIGS. 7A-7C depict flow diagrams of example methods for obtaining a dried blood spot (DBS) sample.
Figure 7B:
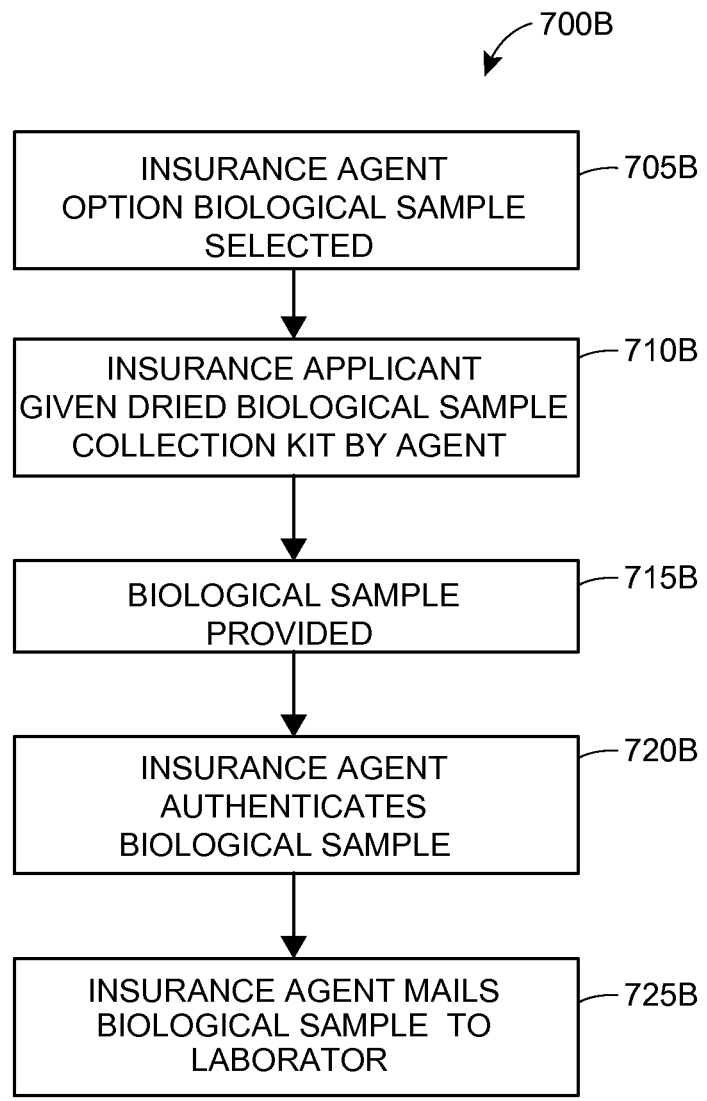
Figure 7C:
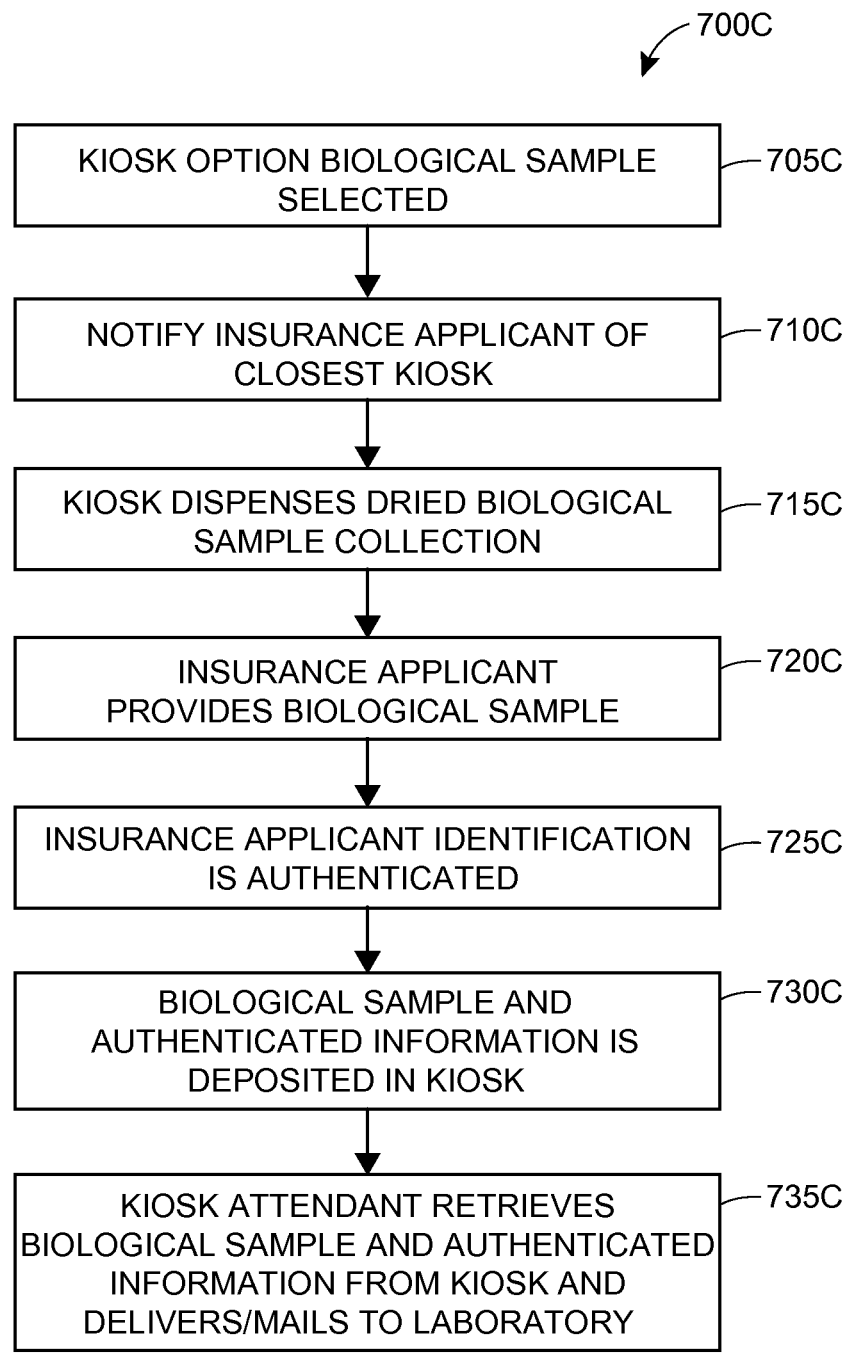

With reference to FIGS. 7A-7C, flow diagrams of example methods 700a, 700b, 700c for obtaining a bio-sample 110, such as dried blood spot (DBS) sample 111, a breath sample 112, an endothelial sample 113 and a saliva sample 114, are depicted. The methods 700a, 700b, 700c may be representative of further detail of the blocks 610-630 of FIG. 6. As depicted in FIG. 7A, when an individual 445a selects to provide in-home bio-sample collection (block 705a), the individual 445a makes a determination as whether he wants a bio-sample collection kit 205a mailed (block 710a). When the individual 445a determines that he does not want a bio-sample collection kit 205a mailed (block 710a), the individual 445a is informed where he may pick-up a bio-sample collection kit 205a and the individual 445a picks-up the kit 205a (block 715a). When the individual 445a determines that he wants a bio-sample collection kit 205a mailed (block 710a), the kit 205a is mailed to the individual 445a (block 720a). Identity authenticating information 115 is provided by the individual 445a (block 725a). For example, the individual 445a may include a lancet 215a with a fingerprint 466a, 467b on the handle 216a or may provide an image or a video 471d (block 725a). The individual 445a may provide a bio-sample 110 (block 730a). The individual 445a may determine whether she wishes to mail in the bio-sample 110 (block 735a). When the individual 445a determines that she wishes to deliver the bio-sample 110 to a laboratory (block 735a), the individual 445a mails or delivers the bio-sample 110 to a laboratory alone with the authenticating information 115 (block 745a). When the individual 445a determines that she does not wish to deliver the bio-sample 110 to the laboratory (block 735a), the individual delivers or mails the bio-sample 110 along with the authenticating information 115 to an insurance Agent (block 740a).

As depicted in FIG. 7B, when an individual 445a selects to have an insurance Agent collect a bio-sample 110 (block 705b), the individual 445a in notified of a location of an insurance Agent's office and the individual 445a is given a bio-sample collection kit 205a at the Agent's office (block 710b). The individual 445a provides a bio-sample 110 to the Agent (block 715b). The Agent provides authenticating information 115 (block 720b). The Agent delivers or mails the bio-sample 110 and authenticating information 115 to a laboratory (block 725b).

As depicted in FIG. 7C, when an individual 445a selects to collect a bio-sample 110 at a kiosk (block 705c), the individual 445a is notified of a location of a kiosk 455a (block 710c) and the individual 445a visits a retail outlet and a kiosk 455a dispenses a bio-sample collection kit 205a (block 715c). The individual 445a provides a bio-sample 110 using the bio-sample collection kit 205a (block 720c). The kiosk 455a provides authenticating information 115 (block 725c). The individual 445a deposits the bio-sample 110 in the kiosk 455a and the kiosk automatically associates the authenticating information 115 with the bio-sample 110 (block 730c). A kiosk attendant 450a delivers or mails the bio-sample 110 and authenticating information 115 to a laboratory (block 735c).

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computerized method for automatically associating an individual with a bio-sample provided by the individual, the method comprising:
   receiving, from the individual, a completed insurance policy application, wherein the completed insurance policy application includes a face-to-face verification between the individual with an approved form of identification;
   providing a bio-sample collection kit to the individual in response to the individual completing the insurance policy application, wherein the bio-sample collection kit includes a lancet, a dried blood spot sample card having filter paper for receiving a bio-sample, and an envelope made from a low gas-permeability material for receiving the dried blood spot sample card, wherein the bio-sample collection kit is for obtaining capillary blood from the individual;
   receiving a bio-sample from the individual using the bio-sample collection kit, wherein the bio-sample includes the capillary blood that is blotted onto filter paper and air dried on the filter paper;
   automatically receiving, using at least one sensor, identifying characteristic data, wherein the identifying characteristic data is representative of at least one identifying characteristic of the individual that provided the bio-sample at a time when the bio-sample is received from the individual, wherein the at least one sensor is selected from: a fingerprint sensor, a hand print sensor, a deoxyribonucleic acid (DNA) sensor, a heart rate electrocardiogram (ECG) sensor, an audio sensor, or an image sensor;
   automatically generating, at a processor of a computing device, identity authenticating data, based on the identifying characteristic data, in response to the processor executing an identity authenticating module, wherein the identity authenticating module includes at least one of: automatic fingerprint identification, automatic handprint identification, automatic deoxyribonucleic acid (DNA) identification, automatic heart rate/electrocardiogram identification, automatic retinal identification, automatic voice recognition, automatic image recognition; and wherein the identity authenticating data associates the individual with the bio-sample; and
   automatically authenticating, using a processor of a computing device, an identity of the individual that provided the bio-sample based on a match between the face-to-face verification and the identity authenticating data.

2. The method of claim 1, wherein the bio-sample collection kit is provided via one of: mailing the bio-sample collection kit to the individual; mailing the bio-sample collection kit to an insurance Agent; dispensing the bio-sample collection kit to the individual via a kiosk; or delivering the bio-sample collection kit to the individual at a retail outlet.

3. The method of claim 1, wherein the bio-sample collection kit is used to collect at least one of: a dried blood spot (DBS) sample; a breath sample; an endothelial sample; or a saliva sample.

4. The method of claim 1, wherein the identity authenticating information is representative of at least one of: a hand print of the individual; a fingerprint of the individual; deoxyribonucleic acid (DNA) of the individual; a heart rate electrocardiogram (ECG) of the individual; retinal characteristics of the individual; voice characteristics of the individual; or visual characteristics of the individual.

5. The method of claim 1, wherein the bio-sample is analyzed using either a laboratory on a chip to obtain biomarker information immediately or using a remote laboratory.

6. The method of claim 1, further comprising:
receiving an analysis of the bio-sample to determine biomarker information; and
automatically generating, by a processor of a computing device, biomarker data based on the identity authenticating data and data representative of the analysis of the bio-sample, the biomarker data is representative of the biomarker information and the identity authenticating data, wherein the biomarker information is representative of at least one of: Albumin; Alkaline Phosphatase; ALT (SGPT); AST (SGOT); Bilirubin (Total); BUN (Blood Urea Nitrogen); Cholesterol; HDL Cholesterol; LDL Cholesterol; Cholesterol/HDL Ratio; LDL/HDL Ratio; Creatinine; Fructosamine; GGT/GGTP; Globulin; Glucose; HIV-1; Total Protein; Triglycerides; CDT; hemoglobin Hb A1c; tobacco use; illicit drug use; Hepatitis B Surface Ag; Hepatitis Be Ag; Hepatitis C Ab; NT-Pro BNP; or PSA.

7. The method of claim 6, further comprising:
generating, using a processor of a computing device, insurance risk data for the individual based, at least in part, on the biomarker data.

8. A system for automatically associating an individual with a bio-sample that is provided by the individual, the system comprising:
an insurance policy application completed by the individual, wherein the completed insurance policy application includes a face-to-face verification between the individual with an approved form of identification;
a bio-sample collection kit provided to the individual in response to the individual completing the insurance policy application, wherein the bio-sample collection kit includes a lancet, a dried blood spot sample card having filter paper for receiving a bio-sample, and an envelope made from a low gas-permeability material for receiving the dried blood spot sample card, wherein the bio-sample collection kit is for obtaining capillary blood from the individual, wherein the individual provides a bio-sample using the bio-sample collection kit;
an identity characteristic data receiving module stored on a memory that causes at least one sensor to automatically receive identifying characteristic data, wherein the identifying characteristic data is representative of at least one identifying characteristic of the individual that provided the bio-sample;
an identity authenticating module stored on a memory that, when executed by a processor, causes the processor to automatically generate identity authenticating data, based on the identifying characteristic data, and to automatically authenticate an identity of the individual that provided the bio-sample based on the identity authenticating data, the identity authenticating data associates the individual with the bio-sample;
a bio-sample analysis module stored on a memory that, when executed by a processor, causes the processor to receive bio-sample analysis data, the bio-sample data is representative of biomarker information; and
a biomarker data generation module stored on a memory that, when executed by a processor, causes the processor to automatically generate biomarker data based on a match between the face-to-face verification and the identity authenticating data and the bio-sample analysis data, the biomarker data is representative of the individual associated with the biomarker information and the identity authenticating data.

9. The system of claim 8, wherein the bio-sample collection kit is provided via one of: mailing the bio-sample collection kit to the individual; mailing the bio-sample collection kit to an insurance Agent; dispensing the bio-sample collection kit to the individual via a kiosk; or delivering the bio-sample collection kit to the individual at a retail outlet.

10. The system of claim 8, wherein the bio-sample collection kit is used to collect at least one of: a dried blood spot (DBS) sample; a breath sample; an endothelial sample; or a saliva sample.

11. The system of claim 8, wherein the identity authenticating information is representative of at least one of: a hand print of the individual; a fingerprint of the individual; deoxyribonucleic acid (DNA) of the individual; a heart rate electrocardiogram (ECG) of the individual; retinal characteristics of the individual; voice characteristics of the individual; or visual characteristics of the individual.

12. The system of claim 8, wherein the bio-sample is analyzed using either a laboratory on a chip to obtain biomarker information immediately or using a remote laboratory.

13. The system of claim 8, wherein the biomarker information is representative of at least one of: Albumin; Alkaline Phosphatase; ALT (SGPT); AST (SGOT); Bilirubin (Total); BUN (Blood Urea Nitrogen); Cholesterol; HDL Cholesterol; LDL Cholesterol; Cholesterol/HDL Ratio; LDL/HDL Ratio; Creatinine; Fructosamine; GGT/GGTP; Globulin; Glucose; HIV-1; Total Protein; Triglycerides; CDT; hemoglobin Hb A1c; tobacco use; illicit drug use; Hepatitis B Surface Ag; Hepatitis Be Ag; Hepatitis C Ab; NT-Pro BNP; or PSA.

14. A non-transitory computer-readable storage medium storing computer-readable instructions that, when executed by a processor, cause the processor to automatically associate an individual with a bio-sample that is provided by the individual, the non-transitory computer-readable storage medium comprising:
an insurance policy application that, when completed by the individual, includes a face-to-face verification between the individual with an approved form of identification;
a bio-sample analysis module that, when executed by a processor, causes the processor to automatically receive bio-sample analysis data in response to the individual completing the insurance policy application, the bio-sample analysis data is representative of biomarker information via a bio-sample collection kit that includes a lancet, a dried blood spot sample card having filter paper for receiving a bio-sample, and an envelope made from a low gas-permeability material for receiving the dried blood spot sample card, wherein the bio-sample collection kit is for obtaining capillary blood from the individual;
an identity characteristic receiving module that causes at least one sensor to automatically receive identifying characteristic data, wherein the identifying characteristic data is representative of at least one identifying characteristic of the individual that provided the bio-sample;
an identity authenticating module that, when executed by a processor, causes the processor to automatically generate identity authenticating data, based on the identifying characteristic data, and to automatically authenticate an identity of the individual that provided the bio-sample based on the identity authenticating data, the identity authenticating data associates the individual with the bio-sample; and a biomarker data generation module that, when executed by a processor, causes the processor to automatically generate biomarker data based on a match between the face-to-face verification and the identity authenticating data and the bio-sample analysis data, the biomarker data is representative of the individual associated with the biomarker information and the identity authenticating data.

15. The computer-readable storage medium of claim 14, wherein the bio-sample collection kit is provided via one of: mailing the bio-sample collection kit to the individual; mailing the bio-sample collection kit to an insurance Agent; dispensing the bio-sample collection kit to the individual via a kiosk; and delivering the bio-sample collection kit to the individual at a retail outlet.

16. The computer-readable storage medium of claim 14, wherein the bio-sample collection kit is used to collect at least one of: a dried blood spot (DBS) sample; a breath sample; an endothelial sample; or a saliva sample.

17. The computer-readable storage medium of claim 14, wherein the identity authenticating information is representative of at least one of: a hand print of the individual; a fingerprint of the individual; deoxyribonucleic acid (DNA) of the individual; a heart rate electrocardiogram (ECG) of the individual; retinal characteristics of the individual; voice characteristics of the individual; or visual characteristics of the individual.

18. The computer-readable storage medium of claim 1, wherein the bio-sample is analyzed using either a laboratory on a chip to obtain biomarker information immediately or using a remote laboratory.

19. The computer-readable storage medium of claim 14, wherein the biomarker information is representative of at least one of: Albumin; Alkaline Phosphatase; ALT (SGPT); AST (SGOT); Bilirubin (Total); BUN (Blood Urea Nitrogen); Cholesterol; HDL Cholesterol; LDL Cholesterol; Cholesterol/HDL Ratio; LDL/HDL Ratio; Creatinine; Fructosamine; GGT/GGTP; Globulin; Glucose; HIV-1; Total Protein; Triglycerides; CDT; hemoglobin Hb A1c; tobacco use; illicit drug use; Hepatitis B Surface Ag; Hepatitis Be Ag; Hepatitis C Ab; NT-Pro BNP; or PSA.

20. The computer-readable storage medium of claim 14, further comprising:

an insurance risk data generation module that, when executed by a processor, causes the processor to generate insurance risk data for the individual based, at least in part, on the biomarker data; and an insurance risk related data storing module that, when executed by the processor of the computing device, causes the processor to store the insurance risk related-data in a memory that is coupled to the processor.

* * * * *